United States Patent [19]

Bergstrand

[11] 4,451,787

[45] May 29, 1984

[54] METHOD AND APPARATUS TO DETECT RANDOMLY DISTRIBUTED DISCONTINUITIES IN DIFFERENT DIRECTIONS IN A LONGITUDINALLY MOVING WEB USING ROTATING PROBES IN OVERLAPPED PATHS

[75] Inventor: Karl-Gunnar Bergstrand, 82 Sikvägen, Frösön, Sweden, S-832 00

[73] Assignees: Karl-Gunnar Bergstrand, Frösön; Bergstrand Kvalitetskontroll AB, Östersund, both of Sweden

[21] Appl. No.: 229,585

[22] PCT Filed: May 9, 1980

[86] PCT No.: PCT/SE80/00135

§ 371 Date: Jan. 7, 1981

§ 102(e) Date: Jan. 7, 1981

[87] PCT Pub. No.: WO80/02594

PCT Pub. Date: Nov. 27, 1980

[30] Foreign Application Priority Data

May 11, 1979 [SE] Sweden ............................. 7904155

[51] Int. Cl.³ ....................... G01N 27/72; G01R 33/12
[52] U.S. Cl. .................................... 324/242; 324/243; 324/262
[58] Field of Search ............... 324/242, 225, 262, 243, 324/239, 240, 238

[56] References Cited

U.S. PATENT DOCUMENTS 3,431,774 3/1969 Dory ..................................... 73/614
3,611,120 10/1971 Forstor ................................. 324/225
4,041,379 8/1977 Karlsson ............................. 324/242

FOREIGN PATENT DOCUMENTS 2636246 2/1973 Fed. Rep. of Germany.
2220950 3/1977 Fed. Rep. of Germany.

Primary Examiner—Gerard R. Strecker
Assistant Examiner—Walter E. Snow
Attorney, Agent, or Firm—Burns, Doane, Swecker & Mathis

[57] ABSTRACT

The invention relates to a method and a device for detecting discontinuities in materials by means of probes sensitive to said discontinuities. According to the invention the material (1) is scanned preferably in the form of a web, by at least two probes (2, 6) which during the scanning sequence are moved above the material (1) in circular paths (3) and (7) in a geometrical plane which is essentially parallel to the geometrical plane of the material web. The circular paths have essentially equal radii and at least one first circular path (3) is arranged in front of a second circular path (7) and is displaced sideways in relation to the second path in such a way that essentially every surface element of the material web is successively covered by at least two circular paths (3) and (7) with such an overlapping that every half-circle segment is sideways overlapped by a consecutive half-circle segment, all seen in the travel direction of the material web.

The invention also relates to a device to carry out the above-mentioned method.

8 Claims, 1 Drawing Figure

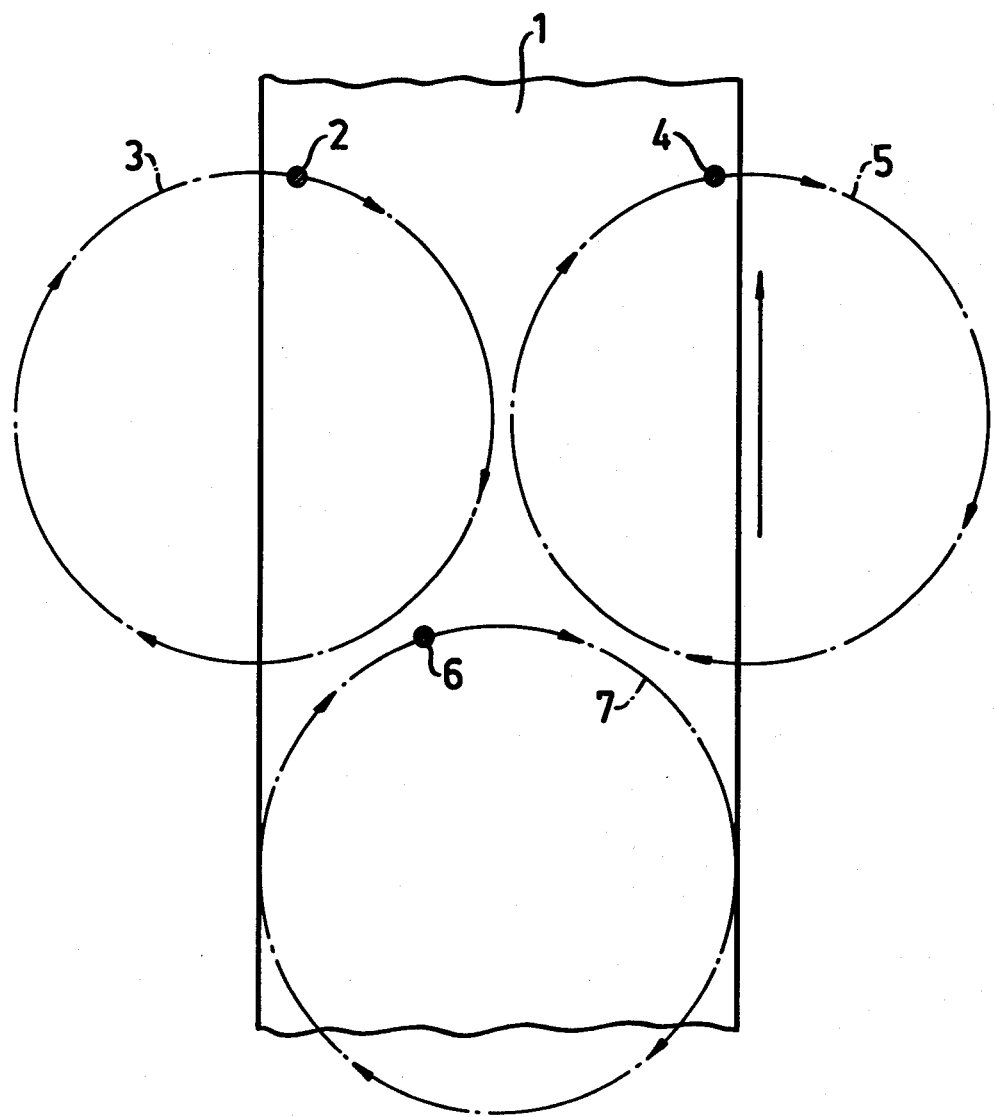

METHOD AND APPARATUS TO DETECT RANDOMLY DISTRIBUTED DISCONTINUITIES IN DIFFERENT DIRECTIONS IN A LONGITUDINALLY MOVING WEB USING ROTATING PROBES IN OVERLAPPED PATHS

This invention relates to a method and an apparatus for detecting discontinuities in materials. Particularly, the invention relates to detecting, by electrical means, such discontinuities as cracks, slag inclusions and similar discontinuities in metallic materials, which chiefly exist in the form of a material web.

Within the industry, the detection of discontinuities in materials is of great importance in the quality control of the materials. In this respect, the materials are scanned by a probe which is sensitive to these discontinuities and reacts to discontinuous changes or jumps in the properties of the material. Then the probe emits a signal. This signal can be processed in different ways, and can, for example, be presented on a display or by a recorder. The signal can also be analysed by a computer in order to make a closer investigation of the discontinuities. Very often the problem is to investigate metallic materials wherein these are scanned by means of a probe which is sensitive to discontinuities in the electromagnetic properties of the material. These electromagnetic discontinuities are produced by the discontinuities of the material when for instance eddy currents are induced in the material or when a magnetic field is applied to the material. However, the invention is not limited to either metallic materials or to electromagnetic detection of the discontinuities.

Thus the invention can, as an example, also be applied for investigation of non-metallic materials by means of ultra-sound and a detector sensitive to ultra-sound, or by reflected laser light.

In modern quality control, it is often necessary tht the testing of the material is continuous in which case the material very often is continuously transported as a web. During this transportation, the material is continuously scanned by one or more probes. In order to accurately detect small discontinuities, it is necessary that the probe cover only a small area in each moment, and in order to cover a larger piece of material, the probe is moved over the material. Alternatively a large number of probes can be used, but practical difficulties limit this number.

In order to increase the sensitivity when using a differential measuring process, and in order to get a signal in a suitable frequency interval, one always wants to move the probe in that direction where the discontinuity has its least extension. Then the probe detects the most pronounced change and this leads to an increased sensitivity. It is easily realized that if the probe is moved along an elongated discontinuity, no pronounced change in the input signal of the probe will be received and this discontinuity could be undetected under unfortunate conditions.

In order to get an efficient scanning of the material when it is continuously moved as a web, one very often wants to move the probe perpendicularly to the moving direction of this web. For example, this is a commonly used method when examining tubes which have an orientation of the discontinuities preferentially in the direction of the axis of the tube. In these cases, the probe rotates around the tube while the tube is moved along the direction of its axis.

If the discontinuities are randomly distributed in the material and have no preferential direction, it is necessary to scan the material in at least two different directions by means of two or more probes in order to detect safely all the discontinuities. One way of achieving this is to let two probes perform an oscillatory movement above the surface of the material perpendicularly to each other. Thus, above the web of the matrial, two probes could oscillate in two directions which each has an angle of 45 degrees to the travel direction of the material and perpendicularly to each other. This procedure is usable at low scanning speeds but with an increased speed, the frequency of oscillation becomes too high in order to completely cover the surface of the material. Mechanically, this solution is also too complicated as the forces of inertia become too high at the turning points of the oscillation.

The present invention avoids the above-mentioned disadvantages and provides an accurate scanning of the web of the material in two different directions in a simple and mechanically uncomplicated way. Also, this invention provides a higher capacity per probe regarding the scanned surface per time unit.

According to the invention, the discontinuities of the material are detected by a probe sensitive to these, wherein the material is transported in the form of a web and at which at least two probes during the scanning, are moved above the web of the material in at least two circular paths, in a plane essentially parallel to the plane of the web of the material and having essentially equal radii and at least one first circular path is arranged in front of a second circular path and is displaced sideways in relation to the second one in such a way that principally every part of the surface of the material web successively is covered by at least two circle paths with such an overlap that each half-circle segment successively is overlapped sideways by a consecutive segment of a half-circle, all seen in the travel direction of the material web.

The invention also relates to an apparatus for carrying out the above-mentioned method and which is characterized in that the apparatus comprises at least two probes arranged to move above the material web in at least two circular paths, the geometrical planes of which are parallel to the geometrical plane of the material web and which have essentially equal radii. At lest one first circular path is arranged in front of a second circular path and displaced sideways compared to the second one in such a way that essentially every part of the surface of the material web successively is covered by at lest two circular paths with such an overlap that each half-circular segment successively is overlapped by a consecutive segment of a half-circle, all seen in the travel direction of the material web.

THE DRAWING

The invention is illustrated more closely by the accompanying drawing which schematically shows a device according to the invention and also shows its function. In the drawing, part of a material web 1 is shown, which is moved in the direction of the arrow. Above the material path 1, the probes 2, 4 and 6 are arranged which are successively moved in the circular paths 3, 5 and 7.

From the drawing it is evident that essentially every surface element of the material web will successively be covered by two halfcircle segments of the circular paths. Thus the right hand half of the material web will be covered by the right hand half-circle segment of the circular path 7 and subsequently by the left hand part of the half-circle segment of the circular path 5. According to this device, essentially every surface element of the material web will be scanned in two directions essentially perpendicular to each other. If for example one considers one point close to the edge of the material web, the probe 6 of circular path 7 will scan this point with a movement principally along the travel direction of the material web, while probe 2 or 4 of circular path 3, respectively 5 will scan the same point at a travel direction principally perpendicular to the travel direction of the material path. It turns out that principally every point of the material path will be scanned in such a manner.

If the two circular paths 3 and 5 adjacent to each other are not tangential to each other, a small area in the middle part will be scanned only by the probe 6 of circular path 7. This fact does not influence the usefulness of the invention as long as the distance between the two circular paths 3 and 5 is small compared to the average size of the discontinuities to be detected. A discontinuity situated in the narrow middle area which is not scanned by any of probes 2 and 4 of circular paths 3 and 5, respectively, will then have a small length perpendicularly to the travel direction of the material web. This discontinuity will then be detected by probe 6 of circular path 7.

In order to scan every surface element of the material web, the minimum velocity of the probes in their circular paths must be in a specific relationship to the travel speed of the material web. This relationship shall be such, that when a probe has made one complete revolution, the material web has been moved maximum the distance corresponding to the extension in the travel direction of the sensing part of the probe. If the travel speed is smaller some overlapping will occur, but at the same time the detecting capacity (covered surface area per time unit) will be reduced. Out of this also comes that the different probes should move with the same velocity in their circular paths.

The radius of the circular paths is not very critical but can be chosen from practical and equipment reasons. When a big radius is used, a larger area can be scanned with a probe but this can also lead to mechanical problems at higher rotational speeds. When using a small radius, higher rotational speeds can be achieved but at the same time the scanned surface area is reduced which means that more circular paths are necessary.

The invention also comprises the possibility to arrange more than one probe in each circular path. These could preferably be evenly distributed along the periphery. By this, the travel speed of the material web can be increased and so the capacity of the apparatus is increased.

The smallest number of probes which can be used according to the invention is two. These are then arranged each in one circular path. These circular paths are arranged so that one is displaced forwardly with for example the double radius and sideways with about one radius, seen in the travel direction of the material web, and the width of the scanned web is maximally the radius of the circle. The displacement between the circular paths in the travel direction of the material web is not very critical. The smallest displacement is best such that the circular paths do not touch each other, but in principle no upper limit exists for this displacement. For wider material webs, more circular paths with probes can be arranged adjacent to each other in two rows across the width of material path, where the centers of the circular paths of the two rows are displaced in such a manner that the centers in the rear row are essentially situated between the centers in the front row. By these means, there is principally no upper limit of the width of the scanned material web.

In the scanning, it is also possible to have the centers of one or more circular paths to make an oscillatory motion perpendicularly to the travel direction of the material web. In this way it is possible to scan a wider area with a probe making one circular path. The frequency of the oscillatory movement must in this case be correlated to the travel speed of the material web, so a complete scanning of the surface is obtained The mechanical construction of an apparatus according to the invention could be made by the use of already known components. Thus the probes may be fitted into rotating discs or rings which together with suitable driving mechanisms, such as electrical motors, may be accomodated into suitable holding fixtures above the material web. When the object is to scan wide material webs, a plurality of discs with probes could be accomodated into a bridge construction above the material web. Preferably the distance of the probes to the material web should be continuously controlled in order to adapt it to different thicknesses of the material web and in order to give the desired sensitivity of the scanning procedure. The probes are connected in manner known per se to suitable devices for signal processing like amplifiers, recorders or picture displays or a computer for analysis and evaluation of the signals. The type of signal processing devices which will be used in each specific case is partly dependent on the actual principle of measurement, partly of the examined material etc. In the light of these factors, one skilled in the art can easily select the proper signal processing method.

The present invention is mainly intended to be used to detect discontinuities in metallic materials and chiefly those in the shape of a strip or web, such as plates or slabs or rolled material of steel, copper, aluminum or other metallic material. Preferably the scanned surface of the material is chiefly planar but also irregular surfaces can be examined according to the invention. As has been emphasized earlier, the invention is not limited only to the examination of metallic materials, but using suitable test principles, also other material types may be examined, such as plastics, paper, etc.

When testing metallic materials, very often electromagnetic test principles are used. Thus, it is common use to induce eddy currents into the metal and detect the magnetic field generated by these eddy currents. Discontinuities in the material will create a sudden change of the detected field and by measuring in different directions and through analysis of the received signals it is possible to estimate the size and shape of the discontinuities or defects. Other test principles which are also based on electromagnetism are also applicable and already known to the expert.

For non-metallic materials could, for example, be used such test methods that are based upon ultra-sound, microwave technique or reflected laser light. The test principle according to the invention is alwyas the same, only with slight modifications of the apparatus in order to suit the applied method of measurement. Probes to be used together with the different methods of measurements are known by the expert and are in many cases available in the market.

Through the present invention, a simple method and a simple device is made available for detecting discontinuities in materials and at which it is guaranteed that essentially every point of the investigated material is scanned in two directions, whereby the discontinuities may be detected independently of their orientation. The invention may also be applied to very different kinds of materials and together with very different principles of measurements. This contributes to facilitate the quality control of the material and make it faster, safer and less expensive.

I claim:

1. A method for detecting laterally, longitudinally and randomly distributed discontinuities in a longitudinally moving web of material by means of probes sensitive to such discontinuities, said method comprising moving a plurality of said probes in circular paths of substantially equal radii across the moving web in planes disposed substantially parallel to the plane of the web, said plurality of probes including at least first and second probes which each define a path of travel across at least a portion of said web, said first and second probes being rotated while mutually displaced longitudinally with reference to the direction of web travel, and while mutually displaced laterally with reference to the direction of web travel by a distance of one radius such that one-half of the circular path of said first probe laterally overlaps one-half of the circular path of the second probe to an extent sufficient to cover at least a portion of the width of said web, the number of said probes being such that the entire width of said web travels past laterally overlapped half-circular paths, the direction of travel of said first probe being different from that of said second probe with respect to a given discontinuity on said web so that such discontinuity is detected in both of said two directions of travel of said probes.

2. The method according to claim 1, wherein the center of the circular path of the first probe is centered over said web with a diameter of said circular path of said first probe being substantially equal to the width of said web, the center of the circular path of said second probe lies over one edge of said web, and the center of the circular path of a third probe lies over the other edge of said web.

3. The method according to claim 1, wherein a plurality of probes are arranged in each circular path.

4. The method according to claim 1, wherein the travelling speed of said web and the rotational speed of said probes are related such that for each complete revolution of a probe, the material web has advanced longitudinally no further than the diameter of the circular path.

5. The method according to claim 1, wherein one of said probes is moved in such direction that the center of its circular path oscillates perpendicularly to the direction of web travel.

6. An apparatus for detecting laterally, longitudinally and randomly distributed discontinuities in a longitudinally moving web of material by means of probes sensitive to such discontinuities, said apparatus comprising a plurality of probes arranged for movement in circular paths of substantially equal radii across the moving web in planes disposed substantially parallel to the plane of the web, said plurality of probes including at least first and second probes which each define a path of travel across at least a portion of said web, said first and second probes being rotated while mutually displaced longitudinally with reference to the direction of web travel, and while being mutually displaced laterally with reference to the direction of web travel by a distance of one radius such that one-half of the circular path of said first probe laterally overlaps one-half of the circular path of the second probe to an extent sufficient to cover at least a portion of the width of said web, the number of said probes being such that the entire width of said web travels past laterally overlapping half-circular paths, the direction of travel of said first probe being different from that of said second probe with respect to a given discontinuity on said web so that such discontinuity is detected in both of said two directions of travel of said probes.

7. The apparatus according to claim 6, wherein the center of the circular path of the first probe is centered over said web with a diameter of said circular path of said first probe being substantially equal to the width of said web, the center of the circular path of said second probe lies over one edge of said web, and the center of the circular path of a third probe lies over the other edge of said web.

8. The apparatus according to claim 8, wherein a plurality of probes are arranged in each circular path.

* * * * *